(12) United States Patent
Davis

(10) Patent No.: US 7,074,987 B2
(45) Date of Patent: Jul. 11, 2006

(54) GENETICALLY-CONTROLLED HERBICIDE RESISTANCE IN COTTON PLANTS IN THE ABSENCE OF GENETIC ENGINEERING

(75) Inventor: William H. Davis, Painview, TX (US)

(73) Assignee: Natural Genes, Inc., Plainview, TX (US)

( * ) Notice: Subject to any disclaimer, the term of this patent is extended or adjusted under 35 U.S.C. 154(b) by 295 days.

(21) Appl. No.: 10/436,158

(22) Filed: May 13, 2003

(65) Prior Publication Data
US 2003/0204866 A1 Oct. 30, 2003

Related U.S. Application Data

(62) Division of application No. 09/782,191, filed on Feb. 14, 2001, now Pat. No. 6,639,124.

(51) Int. Cl.
*A01H 5/00* (2006.01)
*A01H 5/10* (2006.01)

(52) U.S. Cl. .................. 800/300; 800/266; 800/314

(58) Field of Classification Search .............. 800/300, 800/314, 298, 266
See application file for complete search history.

(56) References Cited

U.S. PATENT DOCUMENTS

| 4,971,908 A | 11/1990 | Kishore et al. ............ 536/23.2 |
| 5,145,783 A | 9/1992 | Kishore et al. ............ 800/300 |
| 5,312,910 A | 5/1994 | Kishore et al. ............ 536/23.2 |
| 5,352,605 A | 10/1994 | Fraley et al. ............. 435/418 |
| 5,530,196 A | 6/1996 | Fraley et al. ............. 800/298 |
| 5,633,435 A | 5/1997 | Barry et al. ............. 800/288 |
| 5,858,742 A | 1/1999 | Fraley et al. ............. 435/468 |
| 6,225,114 B1 | 5/2001 | Eichholtz et al. ........ 435/320.1 |
| 6,248,876 B1 | 6/2001 | Barry et al. ............. 536/24.3 |

FOREIGN PATENT DOCUMENTS

GB    2 326 163 A   * 12/1998

OTHER PUBLICATIONS

Jordan et al 1979, Agronomy Journal 71:927-928.*
Regier et al 1986, Crop Science 26(2):376-377.*
Jordan et al., 1979, "*Tolerance of Cotton to the Herbicide Glyphosate*", Agronomy Journal, 71(6): pp. 927 to 928.
Åberg, E. 1964, Chapter 14, The Physiology and Biochemistry of Herbicides, Academic Press, New York, New York, L.J. Audus editor.
Bridger et al. 1994, "*Cold Accilmation Increases Tolerance of Activated Oxygen in Winter Cereals*", Journal of Plant Physiology 144: pp. 235 to 240.
Lee, J.A. 1987, p. 154, Chapter Five, Principles of Cultivar Development, vol. 2, Crop Species, Macmillan Pub. Co., New York, W.R. Fehr editor.

* cited by examiner

*Primary Examiner*—David H Kruse
(74) *Attorney, Agent, or Firm*—Buchanan Ingersoll PC

(57) ABSTRACT

A process is provided for selecting cotton plants which exhibit naturally-occurring genetically-controlled herbicide resistance. Initially cotton seeds are subjected to cold stress (as described) and cotton plants are formed from the seeds that germinate. Seeds are formed following the self-pollination of the resulting plants. These seeds upon maturity are soaked in a liquid containing a herbicide (e.g., a glyphosate) for a period of time sufficient for the herbicide to reach the embryos of the seeds. The seeds following such soaking are planted in a growing medium and produce at least one cotton plant that displays herbicide resistance. The plant is analyzed for the possible presence of a foreign gene for herbicide resistance that would attribute the manifest herbicide resistance to genetic engineering. A cotton plant is selected wherein the herbicide resistance is not attributable to genetic engineering.

5 Claims, No Drawings

GENETICALLY-CONTROLLED HERBICIDE RESISTANCE IN COTTON PLANTS IN THE ABSENCE OF GENETIC ENGINEERING

This is a Divisional Patent Application of U.S. patent application Ser. No. 09/782,191, filed Feb. 14, 2001 (now U.S. Pat. No. 6,639,124, granted Oct. 28, 2003).

BACKGROUND OF THE INVENTION

Cotton, (i.e., plants of the genus *Gossypium*) long has been recognized to be an important crop which is being grown in many parts of the world. This crop is primarily grown for its lint. The seed may be used for planting or as a source of an edible oil with the seed residue serving as a livestock feed.

Modern agricultural practices are increasingly taking advantage of herbicides to eliminate unwanted weeds from cotton fields and to minimize the labor expense of tilling the fields to eliminate weeds. Presently, no selective herbicides that will kill only the major weed species are available for use in cotton fields. Accordingly, it has been necessary in the past to use genetic engineering to genetically modify the cotton plants so that they are resistant to herbicides that are normally non-selective and are effective in controlling the weeds that appear in the growing area. Such herbicide can be applied by spraying to the entire growing area at an appropriate time in the plant's life cycle. Representative weeds that are killed by herbicides in cotton fields include Amaranthis (Pigweed), Russian Thistle, Kochia, Mint Weed, Field Bindweed, Silver Leaf Nightshade, Lambs Quarters, Burr Ragweed, etc.

Genetic engineering has involved the incorporation of a foreign gene for herbicide resistance that is not naturally-occurring in cotton into a chromosome of the cotton plant. Such procedure requires special expertise and tends to be costly. It is necessary to use a promoter that is not naturally-occurring in cotton to be inserted so as to enable the foreign gene for herbicide resistance to be activated in the chromosomes of the cotton plant. A common promoter when incorporating herbicide resistance for glyphosate resistance into cotton is CaMV35S. Other available promoters include ACTIN, NOS, and PCSLV. Representative prior publications that concern the use of genetic engineering to produce such herbicide resistance include U.S. Pat. Nos. 4,971,908; 5,145,783; 5,312,910; 5,352,605; 5,530,196; 5,633,435; and 5,858,742.

It is an object of the present invention to provide a new route for providing genetically-controlled herbicide resistance in cotton plants in the absence of genetic engineering involving the insertion of a foreign gene in cotton plants.

It is an object of the present invention to provide a cotton seed capable of forming a cotton plant having genetically-controlled herbicide resistance that is not attributable to genetic engineering involving the insertion of a foreign gene in cotton plants.

It is an object of the present invention to provide a cotton plant having genetically-controlled herbicide resistance that is not attributable to genetic engineering involving the insertion of a foreign gene in cotton plants.

It is another object of the present invention to provide a new isolated nucleic acid encoding for a protein which when expressed causes herbicide resistance that is naturally-occurring in cotton.

It is another object of the present invention to provide an isolated nucleic acid comprising $HG^g$ gene selected from R418ctHG$^g$hg$^g$ having ATCC Accession No. PTA-2132 which when expressed causes a cotton plant to be glyphosate herbicide resistant, as well as a to provide a vector and plant cell comprising the same.

It is a further object of the present invention to provide a cotton plant having genetically-controlled herbicide resistance that can be sprayed with a herbicide during all phases of the life cycle of the plant without any substantial harm.

These and other objects, as well as the scope, nature and utilization of the claimed invention will be apparent to those skilled in this area of technology from the following detailed description and appended claims.

SUMMARY OF THE INVENTION

A process is provided for selecting a cotton plant which exhibits genetically-controlled herbicide resistance that is not attributable to genetic engineering comprising:
(a) cold stressing cotton seeds in a humid atmosphere,
(b) planting the cotton seeds following step (a) to produce cotton plants,
(c) self-pollinating cotton plants produced in step (b) and forming cotton seeds thereon as the result of the self-pollination,
(d) maintaining the cotton seeds produced in step (c) for sufficient time to reach maturity,
(e) soaking the mature cotton seeds from step (d) in a liquid comprising a herbicide for a period of time sufficient for the herbicide to reach the embryos of the cotton seeds,
(f) planting the cotton seeds following the soaking of step (e) in a growing medium and producing at least one cotton plant that displays resistance to the herbicide,
(g) analyzing a portion of a plant from at least one cotton plant produced in step (f) or a descendant thereof to confirm the absence of a foreign gene for herbicide resistance introduced by genetic engineering, and
(h) selecting a cotton plant from step (g) which exhibits genetically-controlled herbicide resistance that is not attributable to a foreign gene for herbicide resistance introduced by genetic engineering.

A cotton seed is provided that is capable of forming a cotton plant having genetically-controlled glyphosate herbicide resistance that is attributable to the homozygous gene pair $HG^gHG^g$ obtainable from cotton R418ctHG$^g$hg$^g$ having ATCC Accession No. PTA-2132.

A cotton plant is provided having genetically-controlled glyphosate resistance that is attributable to the homozygous gene pair $HG^gHG^g$ obtainable from cotton R418ctHG$^g$hg$^g$ having ATCC Accession No. PTA-2132.

An isolated nucleic acid comprising a $HG^g$ gene derived from cotton R418ctHG$^g$hg$^g$ having ATCC Accession No. PTA-2132 is made possible which when expressed in a cotton plant causes the cotton plant to be glyphosate herbicide resistant. The isolated nucleic acid can be incorporated in a vector and the vector can be incorporated in a plant cell.

DESCRIPTION OF PREFERRED EMBODIMENTS

Normally cotton seeds are adversely influenced when subjected to cold temperatures below 55° F. for any appreciable period of time (e.g., over eight hours). When such cold temperatures are encountered, it is observed that the plants resulting from such seeds commonly exhibit retarded growth, spindly stems, root abnormalities, and failure to reach sexual maturity.

The cotton seeds that are used as the starting material in the process of the present invention are harvested from cotton plants which have not been previously rendered herbicide resistant by the use of genetic engineering through the insertion of a foreign gene for herbicide resistance. In preferred embodiments, the cotton seeds are derived from cotton plants of preexisting cotton varieties or lines which are recognized to display superior agronomic characteristics under conventional cotton growing conditions.

During the initial step of the process of the present invention, the cotton seeds are cold stressed in a humid atmosphere under conditions that normally would be deleterious to such seeds. Representative temperatures within the range of approximately 40 to 50° F. (most preferably approximately 42 to 49° F.) commonly are employed during the cold stressing. If the temperature is above 50° F., many more marginal plants commonly survive and commonly require an excessive number of cold-stressing cycles for removal from the population. If the temperature is below 40° F., there commonly are few surviving plants. During the cold stressing step of the process, day temperatures of approximately 49° F. and night temperatures of approximately 42° F. or a constant temperature of approximately 45° F. have been used to advantage. The duration of the cold stressing step of the process preferably is at least approximately 7 days, and most preferably at least approximately 18 days. Cold stressing of 7 to 18 days has commonly been utilized when practicing the process of the present invention. The desired results are not commonly achieved if the duration of the cold stressing is less than seven days. Colder temperatures for shorter periods of time have proven to be ineffective in research conducted to date. During the cold stressing it is essential that the seeds additionally be subjected to a humid atmosphere. The relative humidity preferably should be at least 90 percent, and most preferably at least 99 percent. The cold stressing optionally can be conducted in a plurality of generations. In a preferred embodiment a plurality of generations (e.g., three generations) of cold stressing are utilized with the progeny of the surviving plants being subsequently cold stressed in each successful generation. This results in a stable population of cold tolerant cotton plants.

At the conclusion of the cold stressing step the seeds are planted, and an effort is made to germinate these to produce cotton plants. It is observed that the cold stressing generally has had a detrimental influence on the ability of most of the seeds to produce typical cotton plants as evidenced by the functional death of the seedling or germination of the seedling combined with an inability to grow to form a normal plant. For instance, some abnormal plants will reach a height of only approximately 6 to 10 inches and will grow no further. Even grow lights will not benefit these plants. Other plants will reach a height of 6 to 10 inches and remain at that height for 2 to 3 weeks prior to resuming normal growth. Maturity will be greatly prolonged because of late flowering and late boll set. A minority of the cold-stressed plants will grow normally and will flower and boll set the same as non-cold-stressed plants. It is these plants that are further used in the process of the present invention. Commonly, only approximately 0.1 to 45 percent of the cotton seeds will germinate to form cotton plants following the cold stressing. The variation in the percentage of cotton plants that grow normally following cold stressing varies with the cotton type that is selected as the starting material. Delta cotton types display only a rare individual plant. The results with West Texas (High Plains) varieties vary greatly. For instance, in tests conducted to date, Paymaster HS-26 had only an approximately 2 percent survival rate, HS-200 had an approximately 8 percent survival rate, JH216 had an approximately 40 percent survival rate, and Tejas had a 42 percent survival rate.

Cotton plants resulting from the germination of the cold-stressed seeds are selected for further use in accordance with the process of the present invention which are observed to demonstrate normal phenotypes and growth characteristics. These plants are subjected to controlled self-pollination and cotton seeds are formed upon the resulting plants that are allowed to mature.

The resulting cotton seeds are harvested and are stored for a sufficient period of time to break the natural dormancy of the seeds. For instance, this can be accomplished by placing the cotton seeds in a freezer at a temperature of 5° F. or less for a minimum of 72 hours and preferably for at least one week.

The mature cotton seeds next are soaked in a liquid comprising a herbicide that normally will kill cotton plants when applied at a concentration at least sufficient to kill unwanted weeds that commonly occur in cotton fields. Representative herbicides include glyphosate, 2,4-dichlorophenoxyacetic acid, glufosinate ammonium butanoic acid, 3,5-dibromo-4-hydroxybenzonitrile, etc.

In a preferred embodiment the herbicide is a glyphosate. Such herbicide is N-(phosphonomethyl)glycine of the chemical formula:

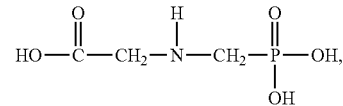

and is commercially available from Monsanto Corporation under the ROUNDUP trademark and other companies under various trademarks. This herbicide is a non-selective, broad spectrum, post-emergence herbicide which is registered for use in more than fifty crops. This molecule is an acid, which dissociates in aqueous solution to form phytotoxic anions. Several anionic forms are known. As used herein, the name "glyphosate" refers to the acid and its anions. Glyphosate inhibits the shikimic acid pathway which provides a precursor for the synthesis of aromatic amino acids. Specifically, glyphosate curbs the conversion of phosphoenolpyruvate and 3-phosphoshikimic acid to 5-enolpyruvyl-3-phosphoshikimic acid by inhibiting the enzyme 5-enolpyruvyl-3-phosphoshikimiate synthase.

The 2,4-dichlorophenoxyacetic acid herbicide commonly is known as "2,4-D" and is commercially available from a number of sources, including United Agri Products, Incorporated. Such herbicide is known to promote very rapid plant growth that is not sustainable.

The glufosinate ammonium butanoic acid herbicide is commercially available from the Aventis Corporation under the LIBERTY trademark.

The 3,5-dibromo-4-hydroxybenzonitrile herbicide commonly is commercially available from the Rhone Poulenc Corporation under the BUCTRIL trademark.

Preferably the cotton seeds are soaked in an aqueous solution of the herbicide. Commonly the herbicide is present in the solution in a concentration of approximately 2 to 6 percent by weight, and most preferably in a concentration of approximately 2.5 percent by weight. Commonly the cotton seeds are simply immersed or suspended in the liquid comprising the herbicide. The soaking of cotton seeds is conducted for a period of time that is at least sufficient for the herbicide to reach the embryos of the cotton seeds. A soaking time of at least 6 hours is preferred and most preferably a soaking time of at least 8 hours is used. Representative soaking times for the cotton seeds commonly are approximately 6 to 12 hours. The liquid comprising the herbicide can be simply provided at room temperature when the cotton seeds are in contact with the liquid and are undergoing such soaking.

Following soaking in the herbicide, the resulting seeds are planted in a growing medium (e.g., soil) and germination of the seeds is attempted to produce cotton plants that display herbicide resistance. The herbicide resistance can be confirmed by spraying the resulting cotton plants with the same herbicide in a concentration typically used to kill weeds growing in a cotton field.

Alternatively, such screening of the resulting cotton plants for herbicide resistance can include the inclusion of the herbicide in the growing medium where the resulting seeds are planted. Good results are obtained in a preferred embodiment when one gallon of a solution containing the herbicide in a concentration of approximately 2 to 6 percent by weight is added to each 4 gallons of soil. The presence of the herbicide in the soil helps to assure that an atypical seed having a harder seed coat has not given a false indication of herbicide resistance by its survival up to the point of germination.

It has been found that a small proportion of the seeds following the cold-stressing, soaking in a liquid comprising a herbicide, and planting in a growth medium, will germinate and yield cotton plants that exhibit resistance to the herbicide. The percentage of the plants that will grow normally at this step in the process has been found to vary from variety to variety. Some varieties have produced no surviving plants in tests to date. Some varieties have produced up to approximately 1 surviving plant per 1,000 seeds, others approximately 1 surviving plant per 5,000 seeds, and others approximately 1 surviving plant per 25,000 seeds. The herbicide resistance of the resulting plants can be further confirmed by another contact (e.g., spraying) with the herbicide. A simple field test kit for herbicide resistance is available from AIT Company of Iroquois, South Dakota, as well as other sources.

A portion of the herbicide-resistant cotton plant produced following such germination or a descendant thereof next is analyzed to confirm that the manifest herbicide resistance is not the result of genetic engineering involving the insertion of a foreign gene that is not naturally-occurring in cotton into the cotton plant by man. This preferably is done by checking for the presence of a promoter that was introduced by man when inserting a foreign gene construct for herbicide resistance. This analysis is used to confirm that the subject cotton plant is not a genetically modified organism and that the manifest herbicide resistance is attributable to a naturally-occurring genetic basis other than that introduced by genetic engineering. More specifically, this analysis is used to confirm that the resulting herbicide-resistant cotton plant or plants were not derived in some manner (e.g., by outcrossing) from a cotton plant that has been genetically engineered for herbicide resistance. In accordance with the process of the present invention a cotton plant is next selected in which the herbicide resistance is under genetic control and in which there is no evidence of the use of genetic engineering to produce the herbicide resistance, such as the presence of a promoter for such herbicide resistance. Any suitable technique can be utilized to confirm the absence of the use of genetic engineering to produce the herbicide resistance. For instance, a DNA-polymerase chain reaction can be utilized. In a preferred embodiment a DNA-polymerase chain reaction is carried out on a portion of a cotton plant leaf. This analysis can be carried out to advantage when analyzing a portion of a young growing leaf. A DNA sequence analysis can be utilized to confirm that the gene for herbicide resistance does not conform to the sequence of a foreign gene inserted into the cotton genome by genetic engineering. For instance, it can be confirmed that the foreign Petunia and CP4 genes heretofore incorporated into commercially available cotton varieties to impart herbicide resistance are absent.

Also, contemplated by the instant invention are the nucleic acids which comprise the genes which when expressed in the cotton plant provide herbicide resistance to that plant. Once a cotton plant which exhibits genetically-controlled herbicide resistance that is not attributable to genetic engineering has been identified, the gene responsible for said naturally-occurring herbicide resistance can be identified. The nucleic acid encoding the gene conferring the naturally-occurring herbicide resistance can then be isolated. The isolated nucleic acid comprises a gene or fragments thereof that encodes a protein responsible for causing the plant to be herbicide resistant. This isolated nucleic acid can then be used to (1) identify other nucleic acids which may contain naturally-occurring mutations that provide herbicide resistance to cotton plants; (2) introduce the isolated nucleic acid into a cotton plant which lacks herbicide resistance by means of genetic engineering which are known to the artisan of ordinary skill; (3) insert the isolated nucleic acid into a suitable vector which can be expressed in a cotton plant; and (4) insert the vector into a plant cell (e.g., a cotton plant cell).

Vectors suitable for use in expressing the nucleic acids, which when expressed in a plant confer herbicide resistance, include but are not limited to pMON979, pMON977, pMON886, pCaMVCN, and vectors derived from the tumor inducing (Ti) plasmid of *Agrobacterium tumefaciens* described by Rogers et al., *Meth. Enzymol.* 153:253–77 (1987). The nucleic acid is inserted into the vector such that it is operably linked to a suitable promoter. Suitable promoters for use with the nucleic acids include CaMV35S, ACTIN, NOS and PCSLV promoters.

The vectors comprising the nucleic acid can be inserted into a plant cell using a variety of known methods. For example, DNA transformation of plant cells include but are not limited to *Agrobacterium*-mediated plant transformation, protoplast transformation, gene transfer into pollen, injection into reproductive organs, injection into immature embryos and particle bombardment. These methods are described more fully in U.S. Pat. No. 5,756,290 and the references cited therein. Site-specific recombination systems can also be employed to reduce the copy number and random integration of the nucleic acid into the cotton plant genome. For example, the Cre/lox system can be used to mediate lox site-specific recombination in plant cells. This method can be found at least in Choi et al., *Nuc. Acids Res.* 28: E19 (2000).

The resulting herbicide resistance is shown to be an infrequently naturally-occurring dominant genetic mutant and not the product of genetic modification. The process steps of the present invention have been found to enable the isolation of such genetic mutant in cotton on a reliable basis. Such herbicide resistance is under genetic control through the expression of one or more dominant gene pairs for herbicide resistance and can be readily transferred to other cotton varieties and lines, particularly when cotton plants are isolated and/or produced by conventional plant breeding.

The herbicide resistance of the present invention can be provided in true-breeding cotton varieties and lines as well as in $F_1$ cotton hybrids. When forming $F_1$ hybrids, the requisite genetic control is provided in both parent plants (e.g., in cytoplasmic male sterile and restorer parent plants). Also, cotton plants can be provided that are resistant to more than one herbicide when appropriate naturally-occurring genes are incorporated into a single cotton plant such as by the use of conventional plant breeding followed by selection.

Heretofore, the use by cotton growers of herbicide resistance (e.g., glyphosate herbicide resistance) produced by genetic engineering has required the application of a herbicide only during the early stages of cotton plant growth and not after the cotton plant has reached the four-leaf stage. For instance, when herbicide-resistant cotton plants of this type are sprayed with a herbicide such as a glyphosate after the four-leaf stage there is deleterious interference with cotton boll production. On the contrary, it has been found that herbicide resistant cotton plants of the present invention can be sprayed with herbicide at any stage of the plant life cycle without deleterious results. For instance, herbicide resistant cotton plants of the present invention can be sprayed with a herbicide following squaring and flowering. A longer and safer period for spraying with a herbicide is provided. Accordingly, a cotton grower when utilizing cotton plants of the present invention, can spray the cotton field with herbicide whenever the need for weed control is apparent without restriction with respect to timing. This provides greater weed control options and flexibility to the cotton grower.

The following Examples are presented as specific illustrations of the claimed invention. It should be understood, however, that the invention is not limited to the specific details of the Examples.

EXAMPLE I

Seeds of cotton B418 (Reg. No. PL-14, PI 583853) were selected as the starting material. This variety was released jointly by the United States Department of Agriculture-ARS and the Texas Agricultural Experiment Station and is publically available. See, *Crop Science*, Vol. 35, No. 5, Page 1518 (1995). The cotton seeds of this variety were obtained from the United States Department of Agriculture at Weslaco, Tex., U.S.A., in 1994.

Approximately 100 grams of seeds of this variety were planted and the agronomic characteristics and boll storm resistance were confirmed to be good. Such plants were allowed to undergo self-pollination and the resulting seeds were harvested.

Seeds of the variety were subjected to cold-stressing in a humid atmosphere for a period of seven days. More specifically, the seeds were placed in porous paper packets, and the packets were placed side by side in a container that was present in a cold cabinet. The packets containing the seeds were contacted at the top and bottom by a damp cotton cloth, and a free end of the cotton cloth was immersed in a container of water. A drainage area was provided at the bottom of the container and the seed packets were suspended above such area for drainage. The temperature within the cold chamber was maintained at a substantially constant 45° F. The relative humidity within the cold cabinet was approximately 99 percent. The seeds next were planted and germination was attempted. Those seeds that germinated formed cotton plants that were self-pollinated to form more cotton seeds. The cold stressing was repeated on the harvested cotton seeds. These cotton seeds were next planted. The seeds that germinated were self-pollinated and cotton seeds were formed thereon. The resulting seeds were harvested and were allowed to mature under dry room temperature conditions.

The mature cotton seeds next were soaked for a period of 6 hours in a 2.5 percent by weight aqueous solution of glyphosate [i.e., N-(phosphonomethyl)-glycine] that was provided at room temperature. This period of time was sufficient for the glyphosate herbicide to reach the embryos of the seeds as evidenced by the failure of many seeds to germinate and the early death of many seedlings resulting therefrom.

Approximately 90,000 cotton seeds next were planted in the field and germination was attempted. The plants that were formed were sprayed with glyphosate herbicide at a rate of 2 pints per acre at the 4-leaf stage and at the 10 to 12 leaf stage. Only 12 cotton plants survived this repeated subjection to the herbicide and displayed true herbicide resistance.

A portion of a young growing leaf from each plant was next subjected to a standard DNA-polymerase chain reaction analysis to confirm the absence of a CaMV35S promoter that if present would attribute the manifest herbicide resistance to genetic engineering. Such promoter was found to be absent in a cotton plant that has been designated R418ctHG$^g$hg$^g$. DNA sequence analysis also has confirmed that this plant lacks the foreign Petunia gene present in commercially available herbicide resistant cotton varieties that are the product of genetic engineering. Genetic studies have shown that the manifest herbicide resistance is attributable to the dominant HG$^g$ gene. This is a naturally-occurring mutant for herbicide resistance that has been discovered through the practice of the process of the present invention. Such gene when found in the heterozygous state can be provided in the homozygous state (i.e., HG$^g$Hg$^g$) through conventional plant breeding followed by selection as will be apparent to those skilled in plant breeding.

On Jun. 27, 2000 a deposit of 2,500 seeds of R418ctHG$^g$hg$^g$ was made under the terms of the Budapest treaty at the American Type Culture Collection, 10801 University Boulevard, Manassas, Va. 20110-2209, U.S.A., and has received ATCC Accession No. PTA-2132. Seeds from this deposit will be irrevocably made available upon the grant of a patent that makes reference to this deposit. However, the availability of these seeds is not to be construed as a license to practice the claimed invention in contravention of rights granted under the authority of any government in accordance with its patent or breeder's right laws.

EXAMPLE II

Example I is substantially repeated with the exception that seeds of cotton B-2-1ct are selected as the starting material. A more widely planted closely related variety derived from this source is JH216. Such starting material had undergone cold stressing prior to soaking in the solution of glyphosate herbicide. Naturally-occurring glyphosate resistance is manifest in a resulting cotton plant designated -B-2-1ctHG$^g$.

EXAMPLE III

Example II is substantially repeated with the exception that 2,4-dichlorophenoxyacetic acid herbicide (i.e., 2,4-D) is substituted for the glyphosate herbicide. Naturally-occurring 2,4-D herbicide resistance is manifest in a resulting cotton plant designated B-2-1ct HG$^{D/D2}$ when sprayed at the 7 to 8-leaf stage with an aqueous 2.5 percent by weight solution of 2,4-D herbicide at a rate of 2 pints per acre.

Cotton plants with 2,4-D herbicide resistance made possible by the present invention will be advantageous to cotton growers where this herbicide is being used to spray nearby corn fields in the event there is unintended herbicide drift.

Although the invention has been described with reference to preferred embodiments, it is to be understood that variations and modifications may be resorted to as will be apparent to those skilled in the art. Such variations and modifications are to be considered within the purview and scope of the claims appended hereto.

I claim:

1. A cotton seed capable of forming a cotton plant having genetically-controlled naturally-occurring glyphosate herbicide resistance that is cotton R418ctHG$^g$hg$^g$ having ATCC Accession No. PTA-2132 or a selfed progeny thereof or an F$_1$ hybrid thereof which display said naturally-occurring glyphosate herbicide resistance.

2. A cotton plant having genetically-controlled naturally-occurring glyphosate herbicide resistance that is cotton R418ctHG$^g$hg$^g$ having ATCC Accession No. PTA-2132 or a selfed progeny thereof or an F$_1$ hybrid thereof which display said naturally-occurring glyphosate herbicide resistance.

3. A method for producing a cotton plant having genetically-controlled naturally-occurring glyphosate herbicide resistance comprising crossing cotton R418ctHG$^g$hg$^g$ having ATCC Accession No. PTA-2132 which displays naturally-occurring genetically-controlled herbicide resistance or a selfed progeny thereof with another cotton plant, and selecting a progeny which displays said naturally-occurring glyphosate herbicide resistance.

4. A method for producing a cotton plant having genetically-controlled naturally-occurring glyphosate herbicide resistance comprising crossing an F$_1$ hybrid of cotton R418ctHG$^g$hg$^g$ having ATCC Accession No. PTA-2132 which displays naturally-occurring genetically-controlled glyphosate herbicide resistance with another cotton plant, and selecting a progeny which displays said naturally-occurring glyphosate herbicide resistance.

5. A method to control weeds in a field comprising the cotton plant according to claim 2 wherein glyphosate is applied to the field at a rate and amount suitable for effective weed control while maintaining the viability of said cotton plant.

* * * * *